United States Patent [19]

Rosenburg

[11] Patent Number: 4,545,941
[45] Date of Patent: Oct. 8, 1985

[54] CO-METATHESIS OF TRIGLYCERIDES AND ETHYLENE

[75] Inventor: Dale W. Rosenburg, Maryville, Mo.

[73] Assignee: A. E. Staley Manufacturing Company, Decatur, Ill.

[21] Appl. No.: 505,616

[22] Filed: Jun. 20, 1983

[51] Int. Cl.[4] .................................. C11C 3/02
[52] U.S. Cl. ........................ 260/410.7; 260/410.8; 585/520
[58] Field of Search ................... 260/410.7, 410.8

[56] References Cited

PUBLICATIONS

Unverified translation of Japanese Kokai 125,317, 11/1976.
W. B. Hughes, "Transition Metal-Catalyzed Homogeneous Olefin Disproportionation" *Organometallics in Chemical Synthesis,* 1, pp. 341-374, (1972).
E. Verkuijlen et al., "Metathesis of Unsaturated Fatty Esters," *Fette-Seifen-Anstrichmitten,* 78, pp. 444-447, (1976).
W. Ast et al., "Olefin-Metathesis of Unsaturated Ethers" *Rec. Trav. Chim.,* 96, pp. M127-M130, (1977).

*Primary Examiner*—Anton H. Sutto
*Attorney, Agent, or Firm*—Forrest L. Collins; James B. Guffey; Philip L. Bateman

[57] ABSTRACT

The co-metathesis reaction of triglycerides having fatty acid esters containing isolated carbon-carbon double bonds and ethylene produces modified triglycerides and alpha-olefins. The reaction occurs at an ethylene partial pressure of about 200 to 550 psig in the presence of a catalytically effective amount of a metathesis catalyst at a temperature of about 100° F. to 500° F.

24 Claims, No Drawings

CO-METATHESIS OF TRIGLYCERIDES AND ETHYLENE

FIELD OF THE INVENTION

This invention relates to the chemical modification of triglycerides and the production of alpha-olefins. More particularly, this invention relates to the co-metathesis reaction of triglycerides having fatty acid esters containing isolated carbon-carbon double bonds and ethylene.

BACKGROUND OF THE INVENTION

A. Triglycerides

Triglycerides are the major component in naturally occurring fats and oils. A triglyceride is the condensation product of one molecule of glycerol with three molecules of fatty acids to yield three molecules of water and one molecule of triglyceride:

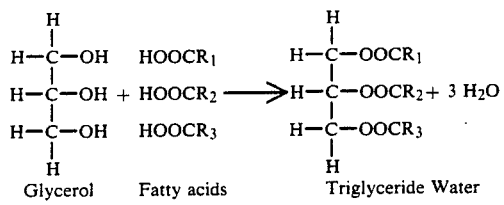

A fatty acid is an aliphatic compound containing 4 to 24 carbon atoms and having a terminal carboxyl radical. Naturally occurring fatty acids, with only minor exceptions, have an even number of carbon atoms and, if any unsaturation is present, the first double bond is generally located between the ninth and tenth carbon atoms. The characteristics of the triglycerides are strongly influenced by the nature of their fatty acid radicals (the components of the triglyceride contributed by the fatty acids are also commonly referred to as esters or simply acids). Some of the more common fatty acid radicals in naturally occurring fats and oils are listed in Tables I and II according to the fatty acid from which they are derived.

TABLE I

| Saturated Fatty Acids | | |
|---|---|---|
| Common Name | Chemical Name | Formula |
| Caprylic | Octanoic | $C_8OOH$ |
| Capric | Decanoic | $C_{10}OOH$ |
| Lauric | Dodecanoic | $C_{12}OOH$ |
| Myristic | Tetradecanoic | $C_{14}OOH$ |
| Palmitic | Hexadecanoic | $C_{16}OOH$ |
| Stearic | Octadecanoic | $C_{18}OOH$ |

TABLE II

| Unsaturated Fatty Acids | | |
|---|---|---|
| Common Name | Chemical Name | Formula |
| Caproleic | 9-Decenoic | $C=C_9OOH$ |
| Lauroleic | 9-Dodecenoic | $C_3=C_9OOH$ |
| Oleic | 9-Octadecenoic | $C_9=C_9OOH$ |
| Linoleic | 9,12-Octadecadienoic | $C_6=C_3=C_9OOH$ |
| Linolenic | 9,12,15-Octadecatrienoic | $C_3=C_3=C_3=C_9OOH$ |

The distribution of the different fatty acid radicals vary among the naturally occuring fats and oils. For example, the distribution by number of fatty acid radicals in soybean triglycerides is about 55% linoleic, 22% oleic, 11% palmitic, 8% linolenic, 3% stearic, and 1% other whereas the distribution in coconut oil is about 48% lauric, 17% myristic, 8% palmitic, 7% capric, 7% caprylic, 5% oleic, 4% stearic, 3% linoleic, and 1% other.

B. Medium Chain Triglycerides

It is well recognized that medium-chain triglycerides, i.e., triglycerides composed primarily of fatty acid esters having a chain length of 6 to 12 carbon atoms, are digested by the body differently than long-chain triglycerides in that they pass from the intestines to the liver via different mechanisms. Apparently due to the different mechanisms of digestion, the medium-chain triglycerides (as opposed to longer-chain triglycerides) are more rapidly metabolized, are less likely to be deposited in fat depots, reduce serum cholesterol levels, and cause a greater caloric intake to be required in order to maintain constant body weight. Accordingly, the use of medium-chain triglycerides in the diet is beneficial to all persons and is especially important to persons suffering from malabsorption syndromes, whether caused by a deficiency of pancreatic lipase, bile salts, or intestinal absorptive area.

In addition to their utility as dietary components, medium-chain triglycerides can easily be converted, via hydrolysis, to medium-chain fatty acids which are suited for a variety of industrial purposes. For example, fatty acids containing 10 carbon atoms are widely used to make oil additives and fatty acids containing 12 carbon atoms are widely used to make soaps and "hard butter".

The primary source of medium-chain triglycerides is by derivation from vegetable oils having high concentrations of $C_6$ to $C_{12}$ fatty acid esters. Preferred sources are coconut oil, which has about 62% medium-chain esters, and palm kernel oil, which has about 54% medium-chain esters. The more plentiful oils, such as soybean oil and corn oil, have virtually no medium-chain esters. To produce a triglyceride rich in medium-chain esters, the coconut or palm kernel oil is first hydrolyzed to form the free fatty acids. The acids are then separated by distillation and the medium-chain fractions are recombined with glycerol to form the medium-chain triglycerides.

Regardless of the chain-length of the triglycerides ingested and the resulting pathway to the liver, the triglycerides are eventually broken down into the constituent fatty acids by the body prior to oxidation. Fatty acids are oxidized by a process known as beta oxidation in which a coenzyme A thioester is first formed and then successive two-carbon acetyl coenzyme A moieties are removed. Upon completion of beta oxidation, a final coenzyme A moiety remains whose structure depends on the nature of the initial fatty acid. If the initial fatty acid has an even number of carbon atoms, regardless of the presence or absence of double bonds, the remaining coenzyme A moiety is another acetyl coenzyme A. If the initial fatty acid has an odd number of carbon atoms and a terminal carbon-carbon double bond, the remaining moiety is acryloyl coenzyme A. If the initial fatty acid has an odd number of carbon atoms and either no double bonds or double bonds anywhere but the terminal position, the resulting moiety is propionyl coenzyme A.

The identity of the resulting coenzyme A moiety can have a very significant effect on the body. For example, acryloyl coenzyme A is believed to be highly toxic.

Therefore, ingestion of a triglyceride containing a fatty acid ester having an odd number of carbon atoms and a terminal carbon-carbon double bond must be avoided. On the other hand, propionyl coenzyne A is converted to succinyl coenzyme A, which is an intermediate in the tricarboxylic acid cycle (also called the Krebs' cycle) along with acetyl coenzyme A. The result of this is that the presence of propionyl coenzyme A actually helps increase the breakdown of acetyl coenzyme A via the tricarboxylic acid cycle. Normally, the body adequately breaks down acetyl coenzyme A. However, diabetics form excessive amounts of acetyl coenzyme A which can overload the cycle and lead to the lethal condition of ketosis. Therefore, the danger of ketosis to a diabetic is reduced if he ingests triglycerides containing fatty acid esters having an odd number of carbons, as long as there is no terminal unsaturation. Unfortunately, odd-number fatty acid esters are quite rare in nature and existing methods of producing such esters are prohibitively expensive.

C. Alpha-Olefins

Alpha-olefins are primarily used as intermediates in the production of polyolefins, chemicals, and consumer products. For example, 1-propene is used to make polypropylene, acrylonitrile, propylene oxide, and isopropyl alcohol. The major uses of 1-butene are to produce poly(1-butene) and various four carbon aldehydes and alcohols. The higher olefins are commonly used in the manufacture of synthetic lubricating oils, detergents, plasticizer alcohols, flavors, perfumes, dyes, pharmaceuticals, and resins. The major commercial source of alpha-olefins is petroleum. Therefore, it is not surprising that the cost of alpha-olefins has risen dramatically in the last decade and some shortages have occurred.

D. Metathesis

Metathesis, also called disproportionation, is a catalytic reaction involving the random interchange of akylidene units among olefinic hydrocarbons via the formation and cleavage of carbon-carbon double bonds. The metathesis reaction occurs between both the same molecules, referred to as self-metathesis or homodisproportionation, as follows:

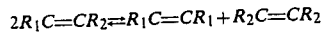

and also between dissimilar molecules, referred to as co-metathesis or heterodisproportionation, as follows:

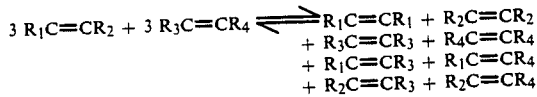

The metathesis reaction is reversible and attains a thermodynamic equilibrium in which distribution of the alkylidene moieties is statistical except when steric or conjugation effects are pronounced. An overview of the metathesis reaction is found in W. B. Hughes, "Transition Metal-Catalyzed Homogeneous Olefin Disproportionation" *Organometallics In Chemical Synthesis*, 1, pp. 341-374 (1972).

E. Co-Metathesis of Fatty Acid Esters and Alkenes

Nakamura, Japanese Kokai Pat. No. 125,317 (1976), describes the co-metathesis of methyl oleate and ethylene to form methyl-9-decenoate and 1-decene. Nakamura states that the reaction occurred under an ethylene pressure of 20 kg/cm$^2$ (about 284 psig) at a temperature of 60° C. (140° F.) over a period of 5 hours. Chlorobenzene was used as the solvent in an amount equal to 3.5 moles chlorobenzene per mole methyl oleate. The yields of methyl 9-decenate and 1-decene were 18 percent each. The co-catalysts employed were tungsten hexachloride and dichloro-ethyl aluminum and each was present at 0.017 moles per mole methyl oleate. Nakamura notes that by careful selection of a suitable ethylene pressure, the formation of the self-metathesis products of methyl oleate was not observed.

In E. Verkuijlen and C. Boelhouwer, "Metathesis of Unsaturated Fatty Esters", *Fette-Seifen-Anstrichmitten*, 78, pp. 444-447 (1976), the authors discuss both the co-metathesis and self-metathesis of fatty acid esters with a catalyst system consisting of equimolar amounts of tungsten hexachloride and tetramethyl tin. In discussing the self-metathesis of fatty esters, the authors note that "the unsaturated fatty oils are excellent starting materials" and discuss the transformation of drying and semi-drying oils, such as linseed oil and soybean oil, into viscous oils. Elsewhere, the authors state that "[c]ometathesis of unsaturated fatty esters with alkenes gives us a powerful tool to produce fatty esters of different chain length. Thus, the cometathesis of methyl oleate and 3-hexene results into 3-dodecene and 9-dodecenoic acid methylester, besides the metathesis products of methyl oleate."

The self-metathesis reaction of 4-pentenyl-butyl-ether, C═C$_4$—O—C$_4$, using a catalyst system of tungsten hexachloride and tetramethyl tin is discussed in W. Ast et al., "Olefin-Metathesis of Unsaturated Ethers", *Rec. Trav. Chim.*, 96, pp. M127-M130 (1977). The authors state that the maximum yield of products was obtained at a reaction temperature of 194° F. and at a catalyst concentration of 0.1 moles tungsten hexachloride per mole olefin and 0.30 moles tetramethyl tin per mole olefin. When the catalyst concentration was reduced to 0.033 and 0.1 moles, respectively, tungsten hexachloride and tetramethyl tin per mole olefin, the yield of products "slightly decreased." Only traces of the products could be detected at 0.01 moles tungsten hexachloride and 0.03 moles tetramethyl tin per mole olefin.

However, nothing in the prior art teaches or suggests the optimum conditions for maximizing the yields from the co-metathesis reaction of triglycerides having fatty acid esters containing isolated carbon-carbon double bonds and ethylene.

SUMMARY OF THE INVENTION

A general object of the invention is to provide an improved process for chemically modifying triglycerides. Another general object of this invention is to provide an improved process for producing alpha-olefins. A more particular object is to provide an improved process for producing triglycerides having reduced chain length fatty acid esters containing isolated and terminal carbon-carbon double bonds.

I have discovered a new and improved process for modifying triglycerides and for producing alpha-olefins. The process comprises reacting triglycerides having fatty acid esters containing isolated carbon-carbon double bonds with ethylene at an ethylene partial pressure of about 200 to 550 psig in the presence of a catalytically effective amount of a metathesis catalyst at a temperature of about 100° F. to 500° F. for a period of time sufficient to convert the fatty acid esters into reduced chain length fatty acid esters containing isolated and terminal carbon-carbon double bonds and to form alpha-olefins.

This process maximizes the yield of products from the co-metathesis reaction of triglycerides having fatty acid esters containing isolated carbon-carbon double bonds with ethylene. As such, this process provides high yields of desirably modified triglycerides and alpha-olefins from a wide variety of readily available sources of triglycerides. The choice of the specific source of reactant triglycerides is determined by the product triglycerides and alpha-olefins desired. For example, medium chain triglycerides are produced from most naturally-occurring fats and oils. Similarly, triglycerides containing odd-numbered fatty acid esters are produced if naturally-occurring fats and oils are modified beforehand to shift certain double bonds.

DETAILED DESCRIPTION OF THE INVENTION

A. The Co-Metathesis Reaction In General

The co-metathesis of triglycerides having fatty acid esters containing isolated carbon-carbon double bonds with ethylene to produce modified triglycerides having reduced chain length fatty acid esters containing isolated and terminal carbon-carbon double bonds and alpha-olefins can be represented as follows:

```
C—OO—CR₁
|
C—OO—Cₓ=Cy     + C=C ——→
|
C—OO—CR₂
```

A triglyceride having a fatty acid ester containing an isolated carbon-carbon double bond        ethylene

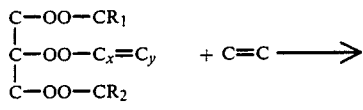

A triglyceride having a reduced chain length fatty acid ester containing an isolated and terminal carbon-carbon double bond        an alpha-olefin where x and y are integers equal to or greater than 2.

The term "isolated" refers to a carbon-carbon double bond which is non-cumulative and unconjugated. In other words, it is a double bond which is separated from another double bond by at least two single bonds. Cumulative and conjugated double bonds are not reactive in the metathesis reaction.

B. Reactant Triglycerides

For use in this invention, the reactant triglycerides must have fatty acid esters containing isolated carbon-carbon bonds. The nature and distribution of these esters determines the products obtained from the co-metathesis reaction.

For example, the most plentiful and inexpensive triglycerides containing such esters are the vegetable oils. All the common vegetable oils contain esters of oleic acid, which is a fatty acid containing an isolated carbon-carbon double bond. When the reactant triglycerides' fatty acid esters comprise esters of oleic acids, the reduced chain length fatty acid esters comprise esters of caproleic acid and the alpha olefins comprise 1-decene:

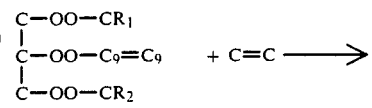

A triglyceride comprising an ester of oleic acid        ethylene

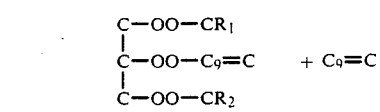

A triglyceride comprising an ester of caproleic acid        1-decene

Another commonly occurring fatty acid ester containing an isolated carbon-carbon double bond is linoleic acid. When the reactant triglycerides comprise esters of linoleic acid, caproleic acid esters are produced along with 1-heptene and 1,4-pentadiene:

```
C—OO—CR₁
|
C—OO—C₉=C₃=C₆     + 2 C=C ——→
|
C—OO—CR₂
```

A triglyceride comprising an ester of linoleic acid        ethylene

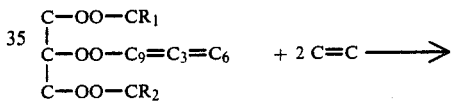

A triglyceride comprising an ester of caproleic acid        1-heptene        1,4-pentadiene Linolenic acid occurs much less frequently in vegetable oils, but soybean oil does have about 8 percent linolenic esters and rapeseed oil has about 5 percent linolenic esters. When the reactant triglycerides comprise esters of linolenic acid, caproleic acid esters are produced along with 1-butene and 1,4-pentadiene.

```
C—OO—CR₁
|
C—OO—C₉=C₃=C₃=C     + 3 C=C ——→
|
C—OO—CR₂
```

A triglyceride comprising an ester of linolenic acid        ethylene

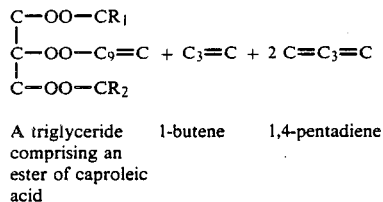

A triglyceride comprising an ester of caproleic acid + 1-butene + 1,4-pentadiene As can be seen, when the reactant triglycerides are unmodified vegetable oils (which all contain oleic acid esters), the products of co-metathesis with ethylene include triglycerides having esters of caproleic acid and 1-decene. The proportion of caproleic acid esters in the modified triglycerides is the sum of the proportions of lauroleic, oleic, linoleic, and linolenic acid esters in the vegetable oils. Similarly, the identity and proportion of the alpha-olefins produced depends on the identity of the vegetable oils' esters.

The modified triglycerides produced from vegetable oil can be used in many different applications. As one example, the modified triglycerides produced from certain vegetable oils can be used directly as medium chain triglycerides in the diet of persons suffering from malabsorption syndromes. The modified triglycerides produced from safflower, sunflower, and soybean oils are especially useful for dietary use since the proportion of potential caproleic acid esters in these triglycerides is high (about 89 percent for safflower and sunflower oils and about 85 percent for soybean oil). As a second example, the modified triglycerides can be hydrolyzed to produce caproleic acid or hydrogenated and then hydrolyzed to produce capric acid. Thirdly, the modified triglycerides can be used for further co-metathesis. For example, metathesis with either 1-butene or 3-hexene would produce acid esters containing 12 carbon atoms. Fourthly, the modified triglycerides can be converted into epoxides by reaction with hydrogen peroxide. The epoxides, in turn, can be hydrated to form polyols, reacted with acrylic acid to produce difunctional acrylates, or reacted with methacrylic acid to form difunctional methacrylates.

A different class of products can be produced if the reactant triglycerides are modified before metathesis. For example, linoleic acid and linolenic acid can be partially hydrogenated to oleic acid and elaidic acid (the trans form of the acid of which oleic acid is the cis form) by control of the hydrogenation conditions. Therefore, triglycerides can be produced from vegetable oils in which nearly all the unsaturated esters are esters of oleic and elaidic acid. As mentioned above, since the sum of oleic, linoleic, and linolenic acid esters in some vegetable oils is quite high, triglycerides can be easily produced which contain very high proportions of oleic and elaidic acid esters. When such triglycerides are co-metathesized with ethylene, the major alpha-olefin produced is 1-decene. Another method of modifying triglycerides before metathesis is to shift the first carbon-carbon double bond from the number nine to the number ten position. When this triglyceride is co-metathesized with ethylene, the resulting triglyceride has a chain length of 11 carbon atoms with a terminal double bond. After hydrogenation, this odd-numbered triglyceride is suitable for use in the diet of diabetics to reduce the danger of ketosis.

C. Ethylene Pressure

The process of the invention is generally carried out at an ethylene partial pressure of about 200 to 550 psig. Co-metathesis occurs at pressures below this range, but the yield of co-metathesis products is reduced. It is believed that the yields decrease because there is less ethylene in solution and, without a sufficient excess of ethylene, the self-metathesis of the triglycerides occurs to an appreciable extent. Similarly, co-metathesis occurs at pressures above this range, but with reduced yields. The reason or reasons for the reduction of yields at high pressures are unknown. Since it would be expected that the yields would continue to increase or, at worst, level off with increasing pressure, the reduction of yields is surprising and unobvious. The maximum yield of the desired co-metathesis products occurs when the ethylene partial pressure is about 330 to 490 psig.

D. Metathesis Catalyst

The co-metathesis reaction of this invention proceeds in the presence of a catalytically effective amount of a metathesis catalyst. The term "metathesis catalyst" includes any catalyst or catalyst system which catalyzes the metathesis reaction.

The metathesis reaction is generally catalyzed by a system containing both a transition and a non-transition metal component. The most active and largest number of catalyst systems are derived from the Group VI A transition metals, tungsten and molybdenum. Organoaluminum compounds, and alkyl derivatives of tin, lithium, and magnesium are the most widely used non-transition metal component of the metathesis catalyst system.

For use in catalyzing the co-metathesis reaction of this invention, the preferred catalyst comprises a tungsten compound and a tin compound. Suitable tungsten compounds include tungsten oxychloride, tungsten pentabromide, tungsten dichloride, tungsten tetrachloride, and tungsten hexachloride. Suitable tin compounds include the alkyl derivatives such as tetramethyl tin and tetra-n-butyl tin. The most preferred metathesis catalyst comprises tungsten hexachloride and tetramethyl tin. To maximize the yields of co-metathesis products, it is preferred that the two catalyst components be present in equimolar amounts and at a concentration of about 0.04 to 0.12 moles of each per mole reactant triglyceride.

E. Solvent

Although the co-metathesis reaction of the invention can be carried out neat, it is preferred that the triglycerides be dissolved in an organic solvent. The presence of a solvent improves mixing and, if added to the triglyceride and partially distilled off before reaction, helps remove traces of water which can poison such metathesis catalysts as tungsten hexachloride. The more commonly used solvents in metathesis reactions include such aliphatic solvents as the saturated hydrocarbons and such aromatic solvents as benzene, chlorobenzene, and toluene. The aliphatic solvents are preferred over the aromatics because of a reduced tendency to interact with the reactants. On the basis of maximizing the yield of co-metathesis products based on a given volume of solvent, the preferred solvents are saturated hydrocarbons boiling in the range of about 125° F. to 250° F., such as commercial hexane. On a molar basis, the preferred amount of solvent is about 0.5 to 5.0 moles per mole triglyceride.

F. Temperature

The reaction is generally carried out at a temperature of about 100° F. to 500° F. The reaction does not proceed to a noticeable degree at temperatures below about 100° F., probably because the energy of activation required for the reaction is not available. The rate of the reactions increases with increasing temperature, but temperatures above about 500° F. are undesirable because the triglycerides begin to degrade. The preferred temperature for the reaction is about 125° F. to 250° F.

G. Yields

This process produces modified triglycerides and alpha-olefins in yields which depend upon the exact conditions employed. Yields of greater than about 30 percent are generally attained and yields of greater than about 60 percent are attained at the preferred conditions. The preferred conditions for the co-metathesis reaction of a vegetable oil and ethylene are as follows: (1) an ethylene partial pressure of about 330 to 490 psig; (2) a catalyst system of 0.04 to 0.12 moles of tungsten hexachloride and tetramethyl tin per mole triglyceride; (3) a saturated hydrocarbon solvent boiling in the range of about 125° F. to 250° F. and present at about 0.5 to 5.0 moles per mole triglyceride; (4) a temperature of about 125 to 250° F.; and (5) a reaction time of greater than about 30 minutes. The process can be carried out batch-wise, semi-batch-wise, or continuously.

H. Examples

The following three examples are illustrative only and were performed using the following general experimental procedures.

A reactor was constructed of 316 stainless steel. The reactor body was a three-inch length of three-inch diameter pipe with plates welded on either end. The body was equipped with a thermometer well and a pressure guage. Stirring was accomplished with a teflon-coated magnet inserted inside the reactor. The top of the reactor was fitted with three openings: (1) a needle valve inlet connected to sources of nitrogen and ethylene gas; (2) a needle valve outlet vented to the atmosphere; and (3) a threaded opening and plug for addition and removal of solids and liquids.

The co-metathesis reaction of soybean oil and ethylene took place as follows: Seventy grams of fully refined (degummed, alkali-refined, water-washed, vacuum-dried, bleached, and deodorized) soybean oil (ca. 0.08 moles) and a solvent were mixed together, partially distilled to remove traces of water, and then poured into the reactor. A given amount of 99%, resublimed tungsten hexachloride and an equimolar amount of tetramethyl tin were then added. The plug was then inserted and stirring was begun. The reactor was then purged successively with nitrogen and ethylene. The reactor was then pressurized with ethylene and heated gradually to a temperature of 220° F. The temperature was maintained for 50 minutes. The reactor was then cooled and the liquid products were poured into a tared flask.

Pure methyl oleate was added to the flask in a known amount to serve as an internal standard. The sample was then analyzed by gas chromatography to determine the yields of 1-heptene and 1-decene.

EXAMPLE 1

This example illustrates that the preferred ethylene pressure in the co-metathesis of soybean oil and ethylene is about 330 to 490 pounds per square inch gauge.

Four reactions were run using ethylene pressures of, respectively, 330, 335, 490, and 660 pounds per square inch guage. The catalyst system used was 0.06 moles tungsten hexachloride and 0.06 moles tetramethyl tin per mole soybean oil. Benzene was employed as the solvent in an amount equal to 3.0 moles benzene per mole soybean oil (after distillation). Other reaction conditions were as described above. The results, shown in Table III, indicate that yields are optimized when the ethylene pressure is between about 330 and 490 pounds per square inch.

TABLE III

| Effect of Ethylene Pressure on Yields in the Co—Metathesis of Soybean Oil and Ethylene | | |
|---|---|---|
| Ethylene Pressure (psig) | Yield of 1-Heptene (%) | Yield of 1-Decene (%) |
| 330 | 61 | 66 |
| 335 | 62 | 70 |
| 490 | 59 | 68 |
| 660 | 44 | 54 |

EXAMPLE 2

This example illustrates that the preferred concentration of the tungsten hexachloride catalyst and the tetramethyl tin co-catalyst in the co-metathesis of soybean oil and ethylene is about 0.03 to about 0.12 moles per mole soybean oil.

Three reactions were run using equimolar amounts of the tungsten hexachloride catalyst and the tetramethyl tin co-catalyst. The amounts used were, respectively, 0.03, 0.06 and 0.12 moles per mole soybean oil. The solvent employed was benzene in an amount equal to 3.0 moles benzene per mole soybean oil. The ethylene pressure was 400 psig. Other reaction conditions were as described above. The results, shown in Table IV, indicate that yields are optimized when the catalyst concentration is between about 0.03 and 0.12 moles catalyst per mole soybean oil.

TABLE IV

| Effect of Catalyst Concentration on Yields in the Co—Metathesis of Soybean Oil and Ethylene | | |
|---|---|---|
| Catalyst Concentration (Moles Tungsten Hexachloride and Tetramethyl Tin per Mole Soybean Oil) | Yield of 1-Heptene (%) | Yield of 1-Decene (%) |
| 0.03 | 17 | 16 |
| 0.06 | 62 | 63 |
| 0.12 | 50 | 42 |

EXAMPLE 3

This example illustrates that hexane is a preferred solvent for the co-metathesis of soybean oil and ethylene.

Three reactions were run using 0.3 milliliters of, respectively, benzene, chlorobenzene, and hexane per gram soybean oil. Tungsten hexachloride and tetramethyl tin were then each added in an amount equal to 0.05 moles per mole soybean oil. The ethylene pressure was 400 psig. Other reaction conditions were as described above. The results, shown in Table V, indicate that hexane is the preferred solvent because the product yields were the greatest when it was used.

TABLE V

Effect of Solvent on Yields in the Co—Metathesis of Soybean Oil and Ethylene

| Solvent | Amount of Solvent (ml/g. oil) | (moles/ mole oil) | Yield of 1-Heptene (%) | Yield of 1-Decene (%) |
|---|---|---|---|---|
| Benzene | 0.3 | 3.0 | 41 | 40 |
| Chlorobenzene | 0.3 | 2.6 | 45 | 55 |
| Hexane | 0.3 | 2.0 | 53 | 56 |

I claim:

1. A process for modifying triglycerides and for producing alpha-olefins which comprises reacting triglycerides having fatty acid esters containing isolated carbon-carbon double bonds with ethylene at an ethylene partial pressure of about 330 to 490 psig in the presence of a catalytically effective amount of a metathesis catalyst at a temperature of about 100° F. to 500° F. for a period of time sufficient to convert the fatty acid esters into reduced chain length fatty acid esters containing isolated and terminal carbon-carbon double bonds and to form alpha-olefins.

2. The process of claim 1 wherein the reaction occurs at a temperature of about 125° F. to 250° F.

3. The process of claim 1 wherein the yield of products is greater than about 30 percent.

4. The process of claim 3 wherein the yield of products is greater than about 60 percent.

5. The process of claim 1 wherein the metathesis catalyst comprises a tungsten compound and a tin compound.

6. The process of claim 5 wherein the tungsten compound and the tin compound are each present at about 0.04 to 0.12 moles per mole triglyceride.

7. The process of claim 6 wherein the metathesis catalyst comprises tungsten hexachloride and tetramethyl tin.

8. The process of claim 1 wherein the triglycerides are dissolved in an organic solvent.

9. The process of claim 8 wherein the organic solvent consists essentially of about 0.5 to 5.0 moles saturated hydrocarbons boiling in the range of about 125° F. to 250° F. per mole triglyceride.

10. The process of claim 1 wherein the reactant triglycerides comprise esters having a chain length of 10 to 24 carbons.

11. The process of claim 10 wherein the reactant triglycerides comprise esters of oleic acid whereby the reduced chain length fatty acid esters comprise esters of caproleic acid and whereby the alpha-olefins comprise 1-decene.

12. The process of claim 11 wherein the reactant triglycerides consist essentially of soybean oil.

13. The process of claim 3 wherein the triglycerides are dissolved in an organic solvent.

14. The process of claim 13 wherein the reactant triglycerides comprise esters having a chain length of 10 to 24 carbon atoms.

15. The process of claim 14 wherein the metathesis catalyst comprises a tungsten compound and a tin compound.

16. The process of claim 15 wherein the reactant triglycerides comprise esters of oleic acid whereby the reduced chain length fatty acid esters comprise esters of caproleic acid and whereby the alpha-olefins comprise 1-decene.

17. The process of claim 16 wherein the reaction occurs at a temperature of about 125° F. to 250° F.

18. The process of claim 15 wherein the tungsten compound and the tin compound are each present at about 0.04 to 0.12 moles per mole triglyceride.

19. The process of claim 18 wherein the yield of products is greater than about 60 percent.

20. The process of claim 19 wherein the reactant triglycerides comprise esters of linoleic acid whereby the reduced chain length fatty acid esters comprise esters of caproleic acid and whereby the alpha-olefins comprise 1-heptene and 1,4-pentadiene.

21. The process of claim 20 wherein the organic solvent consists essentially of about 0.5 to 5.0 moles saturated hydrocarbons boiling in the range of about 125° F. to 250° F. per mole triglyceride.

22. The process of claim 21 wherein the reactant triglycerides comprise esters of linolenic acid whereby the reduced chain length fatty acid esters comprise esters of caproleic acid and whereby the alpha-olefins comprise 1-butene and 1,4-pentadiene.

23. The process of claim 22 wherein the metathesis catalyst comprises tungsten hexachloride and tetramethyl tin.

24. The process of claim 23 wherein the reactant triglycerides consist essentially of soybean oil.

* * * * *